(12) United States Patent
Kiyohara et al.

(10) Patent No.: US 8,542,275 B2
(45) Date of Patent: Sep. 24, 2013

(54) METHOD AND APPARATUS FOR CROSS-SECTION PROCESSING AND OBSERVATION

(75) Inventors: Masahiro Kiyohara, Chiba (JP); Makoto Sato, Chiba (JP); Haruo Takahashi, Chiba (JP); Junichi Tashiro, Chiba (JP)

(73) Assignee: SII Nanotechnology Inc., Chiba (JP)

( * ) Notice: Subject to any disclaimer, the term of this patent is extended or adjusted under 35 U.S.C. 154(b) by 384 days.

(21) Appl. No.: 12/880,626

(22) Filed: Sep. 13, 2010

(65) Prior Publication Data

US 2011/0063431 A1   Mar. 17, 2011

(30) Foreign Application Priority Data

Sep. 15, 2009  (JP) ................................. 2009-213597
Jul. 20, 2010  (JP) ................................. 2010-163036

(51) Int. Cl.
*H04N 7/18*     (2006.01)
(52) U.S. Cl.
USPC ........................................................ 348/80
(58) Field of Classification Search
USPC ........................................................ 348/80
See application file for complete search history.

(56) References Cited

U.S. PATENT DOCUMENTS

| | | | |
|---|---|---|---|
| 2002/0185597 A1* | 12/2002 | Ikku et al. ..................... | 250/309 |
| 2006/0065854 A1* | 3/2006 | Shichi et al. ............. | 250/492.21 |
| 2007/0211327 A1* | 9/2007 | Taniguchi et al. ............ | 359/238 |
| 2008/0189270 A1* | 8/2008 | Takimoto et al. ................. | 707/5 |

FOREIGN PATENT DOCUMENTS

JP          11-273613 A      10/1999

* cited by examiner

*Primary Examiner* — David Czekaj
*Assistant Examiner* — Tracy Li
(74) *Attorney, Agent, or Firm* — Brinks Hofer Gilson & Lione

(57) ABSTRACT

A cross-section processing and observation method includes: forming a first cross section in a sample by etching processing using a focused ion beam; obtaining image information of the first cross section by irradiating the focused ion beam to the first cross section; forming a second cross section by performing etching processing on the first cross section; obtaining image information of the second cross section by irradiating the focused ion beam to an irradiation region including the second cross section; displaying image information of a part of a display region of the irradiation region from the image information of the second cross section; displaying the image information of the first cross section by superimposing it on the image information being displayed; and moving the display region within the irradiation region. Observation images in which display regions are aligned can be obtained while reducing damage to the sample.

7 Claims, 5 Drawing Sheets

METHOD AND APPARATUS FOR CROSS-SECTION PROCESSING AND OBSERVATION

RELATED APPLICATIONS

This application claims priority under 35 U.S.C. §119 to Japanese Patent Application Nos. 2009-213597 filed on Sep. 15, 2009 and 2010-163036 filed on Jul. 20, 2010, the entire content of which is hereby incorporated by reference.

BACKGROUND OF THE INVENTION

1. Field of the Invention

The present invention relates to processing and observation of a sample using a focused ion beam apparatus.

2. Background Art

As a technique for cross-section processing and observation of a sample, such as a semiconductor, a focused ion beam has been used extensively. As an application of this technique, a 3D image of a sample interior is constructed by repetitively performing cross-section processing and observation in a specific region. Initially, a step of forming a cross section in a sample by etching processing using a focused ion beam and a step of obtaining an observation image of the cross section are performed repetitively. This operation is referred to as the cut-and-see operation. Subsequently, a plurality of obtained cross-section observation images are combined. A 3D image can be thus constructed. It is also possible to stop processing when a cross section of a desired observation subject is formed by the cut-and-see operation. A method of determining a processing end point through processing and observation of a sample defect using an FIB (Focused Ion Beam)-SEM (Scanning Electron Microscope) apparatus is disclosed, for example, in JP-A-11-273613.

In order to conduct a comparative examination and perform 3D reconstruction processing using observation images obtained by the cut-and-see operation, it is preferable that display regions in a plurality of observation images are aligned. In a case where an FIB-SEM apparatus is used, there is no need to move a stage during the cut-and-see operation. It is therefore easy to obtain continuous cross-section images in the same display range.

However, because the FIB-SEM apparatus is an expensive apparatus having a complex configuration, there has been a need to enable the cut-and-see operation by a focused ion beam apparatus that is not equipped with a SEM apparatus. On the other hand, in order to enable the cut-and-see operation by a focused ion beam apparatus that is not equipped with a SEM apparatus, there are problems as follows.

When a cross section is formed, processing is performed by irradiating a focused ion beam to a sample in a direction perpendicular to the sample. By contrast, when the cross section is observed, observation is performed by tilting the sample so that a focused ion beam is irradiated to the cross section. In other words, because the sample is tilted between processing and observation, it is necessary to tilt and move a sample stage. As an observation subject becomes finer in recent years, there has been a need for high-resolution cross-section observation. In the cut-and-see operation for high-resolution cross-section observation, displacement of the display regions among a plurality of cross sections caused when the sample stage is tilted and moved is by no means negligible.

In a case where such displacement of the display regions occurs, positioning of the display region is performed in the related art by deflecting a beam to move a beam irradiation position or fine-tuning the position of the sample stage while cross-section observation is performed. The display region is positioned by viewing an observation image being positioned while a charged-particle beam is irradiated to the sample. Hence, a charged-particle beam is kept irradiated to the sample during the positioning.

However, when a charged-particle beam is kept irradiated to the sample, damage is given to the sample. More concretely, contamination adheres to the sample by an interaction of a residual gas inside a vacuum sample chamber and a charged-particle beam, a microstructure in the sample is lost by etching, and the shape of the sample is changed through an irradiation of a charged-particle beam.

SUMMARY OF THE INVENTION

An object of the invention is to provide a method and an apparatus capable of obtaining a plurality of observation images in which display regions are aligned while reducing damage to a sample.

A cross-section processing and observation method according to an aspect of the invention includes: forming a first cross section in a sample by etching processing using a focused ion beam; obtaining image information of the first cross section by irradiating the focused ion beam to the first cross section; forming a second cross section by performing etching processing on the first cross section using the focused ion beam; obtaining image information of the second cross section by irradiating the focused ion beam to an irradiation region including the second cross section; displaying image information of a part of a display region of the irradiation region from the image information of the second cross section; displaying the image information of the first cross section by superimposing the image information of the first cross section on the image information being displayed; and moving the display region within the irradiation region.

According to the cross-section processing and observation method described above, it becomes possible to obtain observation images in which there is no positional displacement of display regions between an image of the first cross section and an image of the second cross section.

A cross-section processing and observation apparatus according to another aspect of the invention includes: a focused ion beam irradiation unit; a sample stage on which to place a sample; a secondary particle detection unit that detects a secondary particle generated from the sample; an image forming unit that forms an observation image according to a signal from the secondary particle detection unit; a storage unit that stores the observation image; a display unit that displays a part of a region of the observation image; and an image editing unit that displays another observation image of the sample read out from the storage unit by superimposing the another observation image on the part of the region of the observation image being displayed on the display unit and moves the part of the region.

According to the cross-section processing and observation apparatus described above, it becomes possible to obtain observation images in which there is no positional displacement of display regions between an image of the first cross section and an image of the second cross section.

The cross-section processing and observation apparatus according to another aspect of the invention may be configured in such a manner that it further includes an image processing unit that extracts a characteristic unit from each of the observation image and the another observation image and superimposes the observation image and the another observation image so that display positions of respective characteristic units coincide with each other.

When configured in this manner, it becomes possible to automatically obtain observation images in which there is no positional displacement of display regions between an image of the first cross section and an image of the second cross section.

According to the invention, positional displacement of the display regions among observation images can be corrected using the obtained image information. It thus becomes possible to obtain a plurality of observation images in which the display regions are aligned while reducing damage to an observation subject.

DETAILED DESCRIPTION OF THE PREFERRED EMBODIMENTS

Hereinafter, an embodiment of the invention will be described on the basis of FIG. 1 through FIG. 5C.

Figure 1:
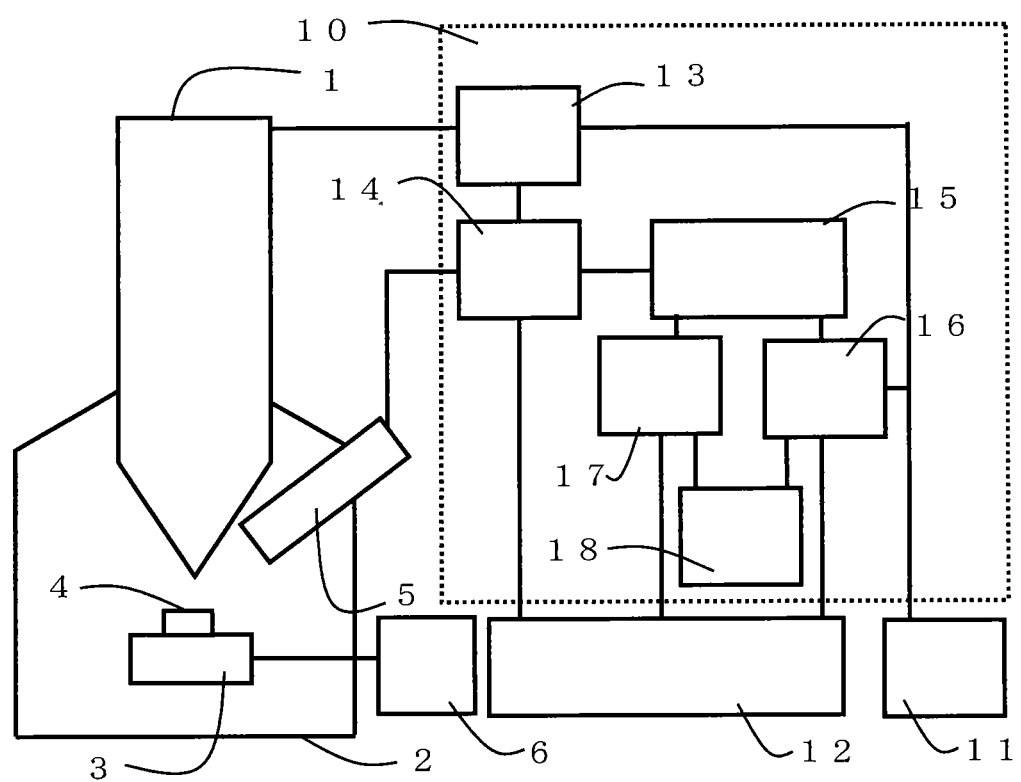
FIG. 1 is a schematic view of a focused ion beam apparatus according to one embodiment of the invention.

As is shown in FIG. 1, a focused ion beam apparatus is configured as follows. That is, the focused ion beam apparatus includes an ion beam column 1 that irradiates a focused ion beam and a sample chamber 2 whose interior is in a vacuum state. The sample chamber 2 has a sample stage 3 on which to place a sample 4 and a secondary electron detector 5 that detects secondary electrons.

The focused ion beam apparatus also includes a sample stage drive unit 6 that tilts the sample stage 3 with respect to a focused ion beam so that a focused ion beam is irradiated to the surface and a cross section of the sample 4.

The focused ion beam apparatus also includes a control unit 10 that controls an irradiation of a focused ion beam and formation of an observation image. The focused ion beam apparatus further includes an input unit 11 serving as an input unit, such as a keyboard and a mouse, used to input an instruction to the control unit 10.

The control unit 10 has an ion beam control unit 13 that controls the ion beam column 1 and an image forming unit 14 that forms image information. The control unit 10 also has a first storage unit 15 that stores image information formed by the image forming unit 14 and an image editing unit 16 that edits image information stored in the first storage unit 15. The control unit 10 also has an image processing unit 17 that performs image processing on image information stored in the first storage unit 15. The control unit 10 further has a second storage unit 18 that stores image information after the image processing by the image editing unit 16 and image information after the image processing by the image processing unit 17.

The focused ion beam apparatus further includes a display unit 12 that displays an observation image of the sample 4 from the image information formed by the image forming unit 14 and image information after the image processing by the image processing unit 17.

Focused ion beam irradiation setting information is inputted into the ion beam control unit 13 from the input unit 11. The ion beam control unit 13 then outputs a scan signal of an ion beam irradiation to the ion beam column 1. The ion beam column 1 accordingly scans and irradiates a focused ion beam to an irradiation region on the surface of the sample 4. Secondary electrons generated from the surface of the sample 4 through the focused ion beam irradiation are detected by the secondary electron detector 5. Image information of the irradiation region is formed by the image forming unit 14 according to a signal of the detected secondary electrons and the scan signal of the focused ion beam irradiation. The image information referred to herein is made up of pixel coordinate information and luminance information of each pixel. The pixel coordinate information is coordinate information of a position at which to irradiate a focused ion beam. The luminance information of each pixel is luminance information of a secondary electron signal generated at a pixel onto which a focused ion beam is irradiated. From the image information formed by the image forming unit 14, image information of a part of the irradiation region is displayed on the display unit 12 as an observation image.

Cross-section processing and observation by the focused ion beam apparatus configured as above will now be described on the basis of FIG. 2A through FIG. 5C.

FIG. 2A through FIG. 2H are schematic views of cross-section processing and observation according to one embodiment of the invention. FIGS. 2A, 2C, 2E and 2G are cross sections of the sample stage 3 and the sample 4. FIGS. 2B, 2D, 2F, and 2H are observation views obtained by scanning and irradiating a focused ion beam 30 from the direction of the focused ion beam 30 in FIGS. 2A, 2C, 2E, and 2G, respectively.

Figure 2A:
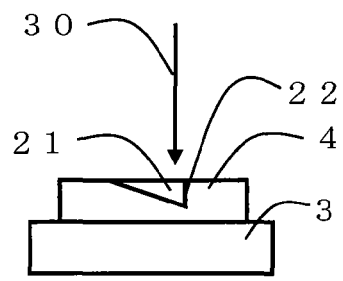
FIGS. 2A through 2H are schematic views of cross-section processing and observation according to one embodiment of the invention.
Figure 2B:
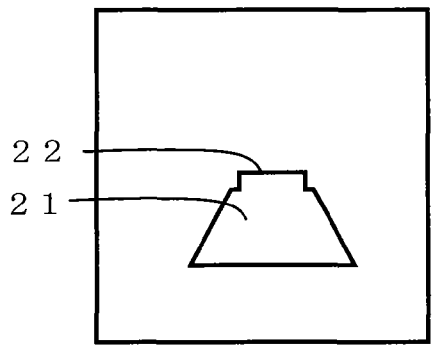

Initially, a cross section is formed for cross-section observation. A concave unit 21 is formed by irradiating the focused ion beam 30 (FIG. 2A). An observation image is then obtained by scanning and irradiating the focused ion beam 30 to an irradiation region of the sample 4 in a direction substantially perpendicular to the surface of the sample 4 (FIG. 2B).

In cross-section observation, observation is performed on a first cross section 22 formed on a side wall of a unit corresponding to the upper side of a trapezoid, which is the shape of the concave unit 21. Herein, it is preferable to select a cross section position in such a manner that the cross section is placed in a direction substantially perpendicular to the surface of the sample 4 and also in a direction substantially perpendicular to an alignment direction of structures that are an observation subject inside the sample 4. The alignment direction referred to herein is a direction in which, for example, vias are disposed repetitively. Also, it is preferable that a proceeding direction of cross-section processing in which cross-section processing and observation are performed repetitively is substantially parallel to a direction in which the structures inside the sample 4 are placed. When configured in this manner, by combining cross-section observation images obtained as the cross-section processing is proceeded, it becomes possible to reconstruct a 3D image of the structures as an observation subject.

A shape of the concave unit 21 will now be described. By forming the concave unit 21 in a trapezoidal shape having the first cross section 22 on the upper side, it becomes possible to collect secondary electrons generated from the first cross section 22 efficiently into the secondary electron detector 5. Also, the concave unit 21 is formed to become deeper on the first cross section 22 side and shallower with distances from the first cross section 22. When configured in this manner, a processing amount can be reduced in comparison with a case where the entire concave unit 21 is formed deep. It should be appreciated, however, that the concave unit 21 is not limited to this shape.

Figure 2C:
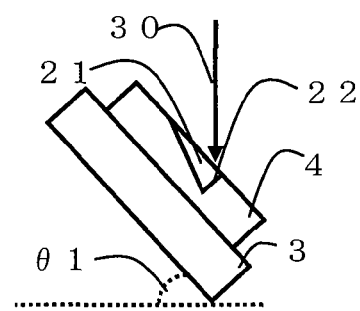
Figure 2D:
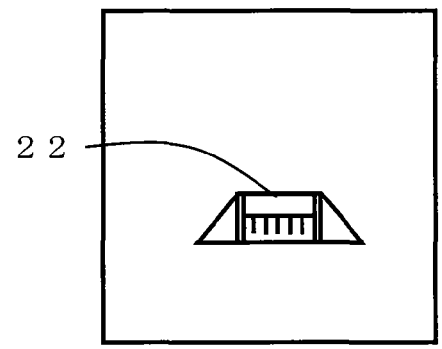

Subsequently, the first cross section 22 is observed. In order to irradiate the focused ion beam 30 on the first cross section 22, the sample stage 3 is tilted. A tilt angle in this instance is θ1. The focused ion beam 30 is then scanned and irradiated to an irradiation region including the first cross section 22 to observe the first cross section 22 (FIG. 2C). The internal structure of the sample 4 appears in the observation image of the first cross section 22 (FIG. 2D).

It should be noted that a beam current of the focused ion beam 30 used during observation is a beam current smaller than a beam current used during etching processing of the concave unit 21. When configured in this manner, it becomes possible to reduce damage given to the first cross section 22 when cross-section observation is performed.

Figure 2E:
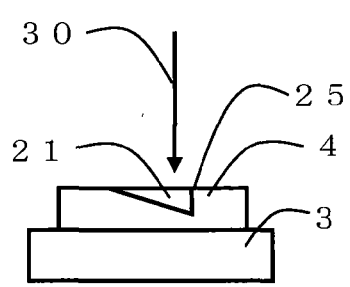
Figure 2F:
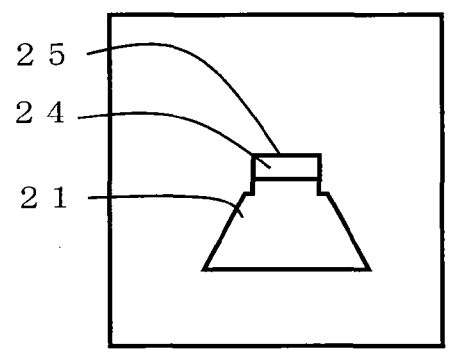

Subsequently, a second cross section is formed. In order to irradiate the focused ion beam 30 in a direction substantially perpendicular to the surface of the sample 4, the tilt of the sample stage 3 is returned to the original degree (FIG. 2E). A concave unit 24 including the first cross section 22 is then formed by etching processing (FIG. 2F). A side surface of the concave unit 24 thus formed is a second cross section 25.

Figure 2G:
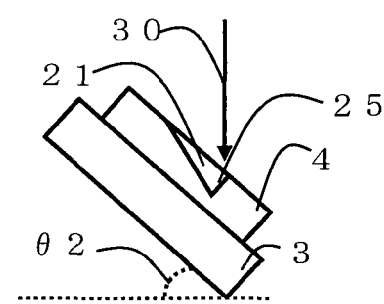
Figure 2H:
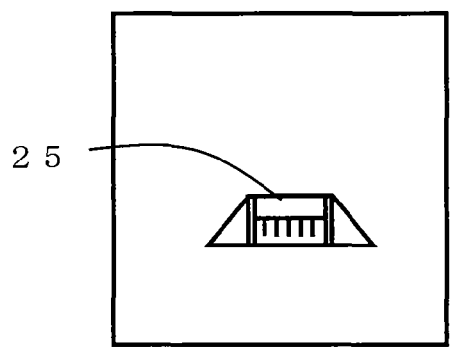
Figure 3:
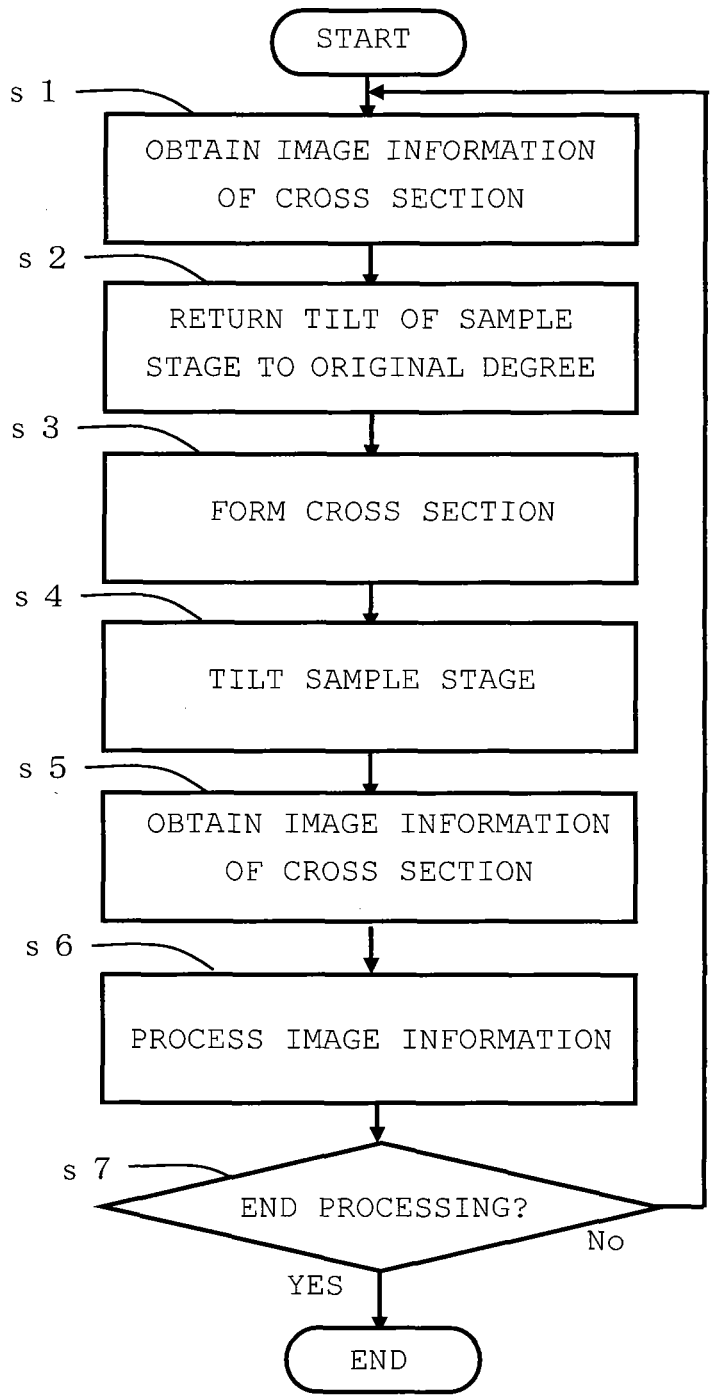
FIG. 3 is a flowchart according to one embodiment of the invention.

Subsequently, the second cross section 25 is observed. In order to irradiate the focused ion beam 30 to the second cross section 25, the sample stage 3 is tilted. A tilt angle in this instance is θ2 (FIG. 2G). The focused ion beam 30 is scanned and irradiated to an irradiation region including the second cross section 25 to observe the second cross section 25 (FIG. 2H). Image information of a plurality of cross sections is obtained by repetitively performing the cross-section formation and the cross-section observation described above.

Incidentally, in cross-section processing and observation, the observation sample stage 3 is tilted repetitively in order to form a cross section and observe the cross section. Eventually, displacement of the tilt angle of the sample stage 3 occurs. The term, "displacement of the tilt angle", referred to herein means an angular difference between the tilt angle θ1 of FIG. 2C and the tilt angle θ2 of FIG. 2G. In cross-section processing and observation to obtain several hundreds of cross section images at resolution in the order of several nanometers, displacement of the tilt angle of the sample stage 3 can cause positional displacement of observation regions among a plurality of obtained cross-section images, which makes it impossible to observe a desired region. In the invention, however, it should be noted that the positional displacement of the observation region is corrected by processing image information.

Processing of image information will now be described. Firstly, a manner in which to obtain image information will be described using the flowchart of FIG. 3. Initially, image information of the first cross section 22 is obtained (s1). The obtained image information is stored in the first storage unit 15. Subsequently, the tilt of the sample stage 3 is returned to the original degree (s2). The concave unit 24 is then formed to expose the second cross section 25 (s3). Subsequently, the sample stage 3 is tilted to observe the second cross section 25 (s4). Image information of the second cross section 25 is thus obtained (s5). The image information of the second cross section 25 is then edited by the image editing unit 16 (s6).

Figure 4A:
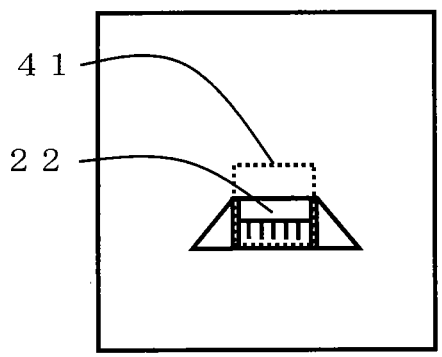
FIGS. 4A through 4E are views used to describe a manner in which to edit image information according to one embodiment of the invention.
Figure 4B:
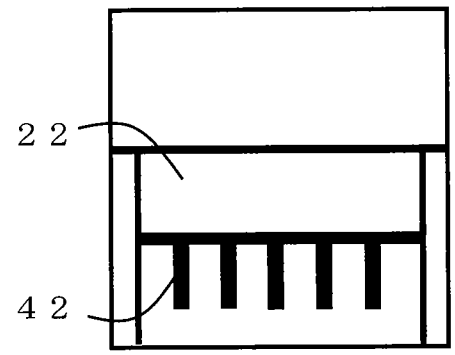

Editing of image information will now be described using FIGS. 4A through 4E. FIG. 4A is an observation image of the first cross section 22. In cross-section observation, image information of an observation region, which is the enlarged first cross section 22, is obtained. A display region 41 is a display region displayed on the display unit 12. FIG. 4B is an observation image of the first cross section 22 within the display region 41. The internal structure, such as vias 42, is exposed to the first cross section 22.

Figure 4C:
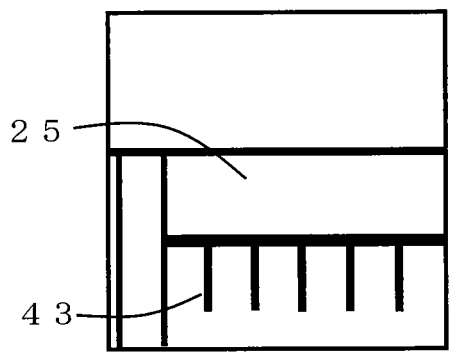

FIG. 4C is an observation image of the second cross section 25 displayed on the display unit 12. To be more concrete, it is an observation image obtained by irradiating the focused ion beam 30 to the position coordinate same as that of the display region 41 of the first cross section 22. Vias 43 are vias same as the vias 42 in the first cross section 22. They are, however, exposed to the corresponding cross sections in different shapes.

Processing as follows is performed by the image editing unit 16. That is, the image information of the first cross section 22 is read out from the first storage unit 15 while the observation image of the second cross section 25 is displayed on the display unit 12. The read image information of the first cross section 22 is superimposed on the observation image of the second cross section 25 on the display unit 12. In this instance, it is preferable that the image information of the first cross section 22 is displayed in the form of a translucent image, so that the observation image of the second cross section 25 is recognizable even when the image information of the first cross section 22 is superimposed thereon. A superimposing method can be, for example, a method of finding an exclusive OR of luminance information of two images for each pixel or a method of displaying image information of two cross sections alternately pixel by pixel.

Figure 4D:
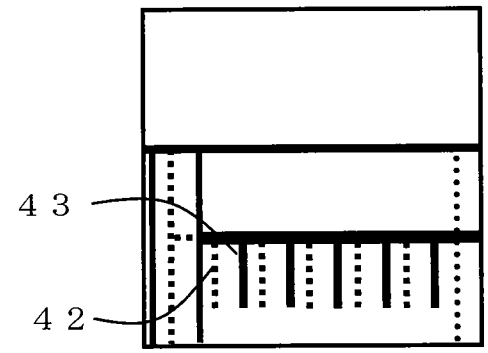
Figure 4E:
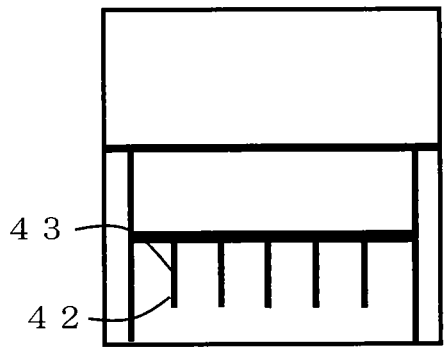

FIG. 4D is an observation image obtained by superimposing the image information of the first cross section 22 on the observation image of the second cross section 25. The internal structure of the cross section 25 is indicated by a dotted line. In FIG. 4D, the positions of the vias 42 and the vias 43 are displaced. This positional displacement is caused by the tilting operation of the sample stage 3. In order to eliminate this inconvenience, the display region of the second cross section 25 is moved in such a manner that the vias 43 are superimposed on the vias 42. Consequently, as is shown in FIG. 4E, the internal structure of the first cross section 22 and the internal structure of the second cross section 25 are superimposed and the display regions of the two cross sections are aligned in the resulting cross-section image.

The display region is moved manually by an operator or automatically by image recognition. In the former case where the display region is moved manually by an operator, the operator inputs an instruction to move the display region in the second cross section 25 from the input unit 11 while viewing the observation view displayed on the display unit 12. In the latter case where the display region is moved automatic processing, image processing is performed by the image processing unit 17.

The image processing is to perform pattern matching by extracting a characteristic unit in the luminance information from each of two pieces of the image information. The image information of the first cross section 22 stored in the first storage unit 15 and the image information of the second cross section 25 are inputted into the image processing unit 17. Pattern matching processing is then performed by the image processing unit 17. The image information of the second cross section 25 obtained by moving the display region obtained by the pattern matching processing is stored in the second storage unit 18.

In the description above, the internal structure exposed to the cross section is used as the characteristic unit. The shape of the internal structure, however, may change depending on which plane the internal structure is cut through. It is therefore preferable to extract a structure of a constant shape as the characteristic unit.

Also, in the description above, the image information of the first cross section 22 is used to correct the display region. The invention, however, is not limited to this configuration. To be more concrete, image information of any cross section formed earlier than the cross section that needs a correction of the display region can be used to correct the display region.

By repetitively performing the steps described above, it becomes possible to obtain image information of a plurality of cross sections in which the display regions are corrected. The image information of the cross sections in which display regions have been corrected is stored in the second storage unit 18. By using a plurality of pieces of the stored image information, a 3D image of the cross-section processed region can be reconstructed.

Figure 5A:
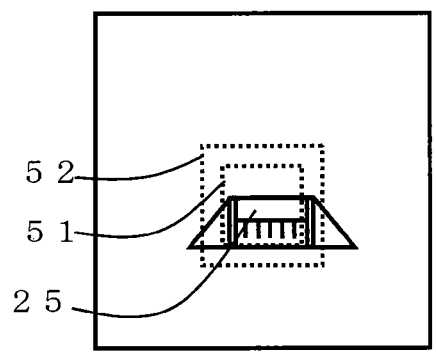
FIGS. 5A through 5C are views used to describe a manner in which to correct a display region according to one embodiment of the invention.
Figure 5B:
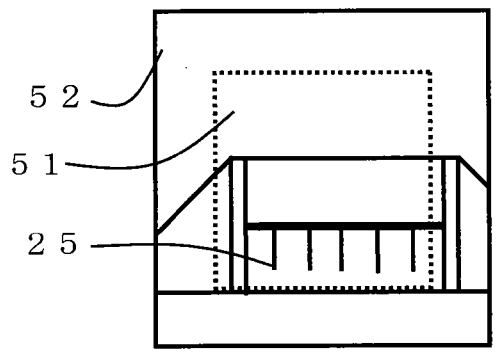
Figure 5C:
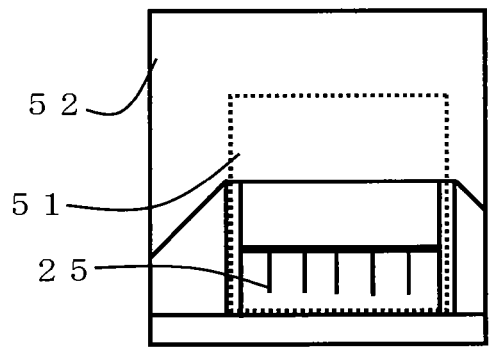

The correction of the display region will now be described using FIGS. 5A through 5C. FIG. 5A is an observation image of the second cross section 25. A display region 51 is a region corresponding to the display region 41 of the first cross section 22. In short, the display region 51 and the display region 41 have the same position coordinate at which to irradiate the focused ion beam 30. When cross-section observation is performed, the focused ion beam 30 is irradiated to a beam irradiation region 52 including the display region 51 and larger than the display region 51 to obtain the image information. The image information thus obtained is stored into the first storage unit 15.

Subsequently, in a case where the display region is corrected manually by the operator, the display region is corrected in the image editing unit 16. To be more concrete, the image information of the beam irradiation region 52 is read out from the first storage unit 15. Upon receipt of an input from the input unit 11, the display region 51 is moved within the beam irradiation region 52 and the image information within the display region 51 thus moved is displayed on the display unit 12. In other words, the display region 51 shown in FIG. 5B is moved within the beam irradiation region 52 until the display region 51 is moved to the position specified in FIG. 5C. The image information in which the display region has been corrected is stored into the second storage unit 18.

In a case where the display region is corrected automatically by image recognition, the display region is corrected in the image processing unit 17. To be more concrete, the image information of the beam irradiation region 52 is read out from the first storage unit 15. The image processing is performed in the image processing unit 17 and the corrected image information is stored into the second storage unit 18.

In the description above, a secondary electron image, which is obtained by irradiating the focused ion beam 30 to obtain the cross section image, is used. It is, however, also possible to use a secondary electron image obtained by irradiating an electron beam.

What is claimed is:

1. A cross-section processing and observation method in a focused ion beam apparatus, the method comprising:
    positioning a sample in the focused ion beam apparatus and forming a first cross section in the sample by etching processing using a focused ion beam;
    obtaining an observation image of the first cross section by irradiating the first cross section with the focused ion beam;
    forming a second cross section by etching the first cross section using the focused ion beam;
    obtaining an observation image of the second cross section by irradiating the focused ion beam on an irradiation region including the second cross section;
    displaying portional image information of a part of a display region of the irradiation region from the observation image of the second cross section;
    displaying image information of the first cross section by superimposing a translucent image of the observation image of the first cross section on the portional image information; and
    moving the display region within the irradiation region, and obtaining observation images of the sample without positional displacement of display regions between the observation image of the first cross section and the observation image of the second cross section.

2. The cross-section processing and observation method according to claim 1, wherein: formation of the second cross section and obtaining of the observation image are performed repetitively.

3. The cross-section processing and observation method according to claim 1, wherein: when the first cross section is formed, the first cross section is formed to be substantially perpendicular to an alignment direction of structures as an observation subject in the sample and substantially perpendicular to a surface of the sample.

4. A cross-section processing and observation apparatus, comprising:
    a focused ion beam irradiation unit;
    a sample stage on which to place a sample;
    a secondary particle detection unit that detects a secondary particle generated from the sample upon exposure to an ion beam from the focused ion beam irradiation unit;
    an image forming unit that forms a first observation image according to a signal from the secondary particle detection unit;
    a storage unit that stores the first observation image;
    a display unit that displays a part of a region of the first observation image; and
    an image editing unit that displays a second observation image of a second cross section of the sample read out from the storage unit by superimposing the second observation image on a translucent image of the part of the region of the first observation image of a first cross section being displayed on the display unit and moves the part of the region,
    wherein the second cross section comprises a focused ion beam-etched section of the first cross section.

5. The cross-section processing and observation apparatus according to claim 4, further comprising:
    an image processing unit that extracts a characteristic unit from each of the first observation image and the second observation image and superimposes the first observation image and the second observation image so that display positions of respective characteristic units coincide with each other.

6. The cross-section processing and observation method according to claim 1, wherein the irradiation region of the focused ion beam is larger than a display region of the first cross section.

7. The cross-section processing and observation method according to claim 4, wherein an irradiation region of the focused ion beam is larger than a display region of the first cross section.

* * * * *